United States Patent

Sugii et al.

[11] Patent Number: 5,266,371
[45] Date of Patent: Nov. 30, 1993

[54] ADHESIVE DRESSING SHEET

[75] Inventors: Tetsuji Sugii; Shintaro Wada; Masayuki Konno, all of Osaka, Japan

[73] Assignee: Nitto Denko Corporation, Osaka, Japan

[21] Appl. No.: 938,684

[22] Filed: Sep. 1, 1992

Related U.S. Application Data

[63] Continuation of Ser. No. 746,009, Aug. 12, 1991, abandoned, which is a continuation of Ser. No. 364,035, Jun. 9, 1989, abandoned.

[30] Foreign Application Priority Data

Aug. 11, 1988 [JP] Japan .................. 63-106557

[51] Int. Cl.$^5$ ............................................ A61F 13/02
[52] U.S. Cl. .................................. 428/40; 428/41; 428/43; 428/131; 428/137; 428/138; 428/213; 428/215; 428/216; 428/219; 428/343; 428/352; 428/354; 428/423.1; 428/452; 602/43; 602/52; 602/57
[58] Field of Search .............. 428/40, 41, 43, 352, 428/354, 343, 131, 137, 138, 213, 219, 423.1; 602/57, 52, 43

[56] References Cited

U.S. PATENT DOCUMENTS

| | | | |
|---|---|---|---|
| 2,576,367 | 12/1951 | Curtis et al. | 424/447 |
| 3,349,765 | 10/1967 | Blanford | 602/57 |
| 4,268,566 | 5/1981 | Ebert | 428/40 |
| 4,306,551 | 12/1981 | Hymes | 424/448 |
| 4,706,662 | 11/1987 | Thompson | 602/57 |
| 4,753,232 | 6/1988 | Ward | 128/156 |
| 5,052,381 | 10/1991 | Gilbert | 602/57 |

FOREIGN PATENT DOCUMENTS

| | | | |
|---|---|---|---|
| 0081989 | 6/1983 | European Pat. Off. | 428/448 |
| 0189999 | 1/1985 | European Pat. Off. | 428/447 |
| 0144891 | 6/1985 | European Pat. Off. | 428/448 |

Primary Examiner—Ellis P. Robinson
Assistant Examiner—Nasser Ahmad
Attorney, Agent, or Firm—Sughrue, Mion, Zinn, Macpeak & Seas

[57] ABSTRACT

An adhesive dressing sheet is disclosed, comprising a polymer film having a high flexibility, an adhesive layer provided on one side of the polymer film, a peeling liner temporarily provided on the adhesive layer, and a flexible sheet on the other side of the polymer film, wherein a bending line is provided on the peeling liner in a direction almost at right angles to the peeling direction of the liner, and the flexible sheet has self supporting properties such that when the liner is peeled off up to the bending line and bent, the liner bending piece does not expand to an angle of 90° or more.

8 Claims, 3 Drawing Sheets

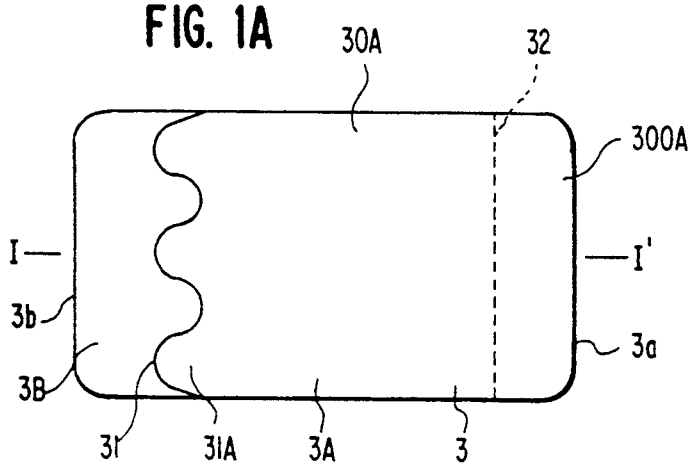
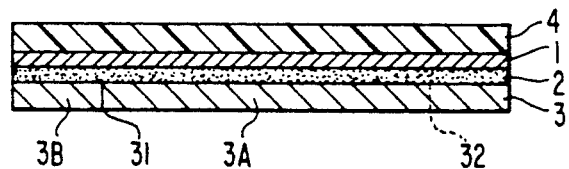
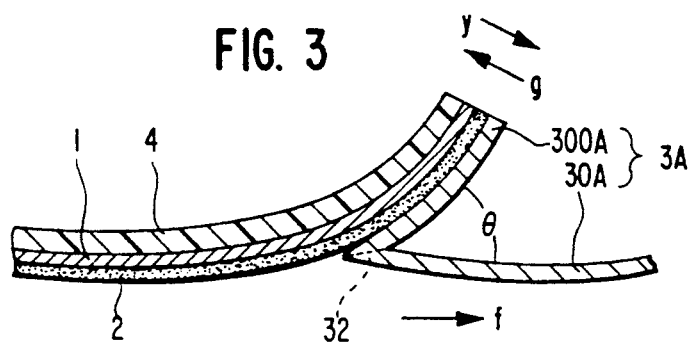
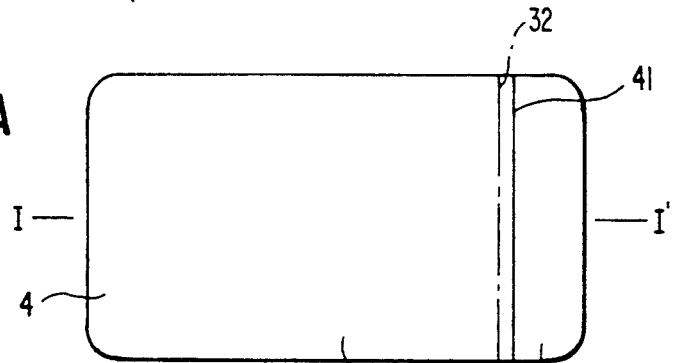
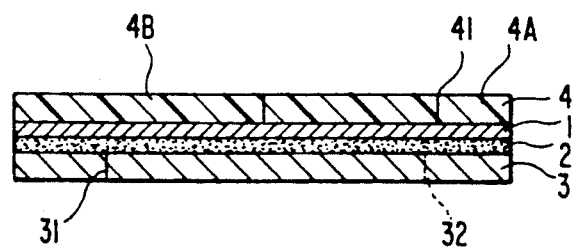

ADHESIVE DRESSING SHEET

This is a continuation of application Ser. No. 07/746,009 filed Aug. 12, 1991, now abandoned which is a continuation of application Ser. No. 07/364,035 filed Jun. 9, 1989, now abandoned.

FIELD OF THE INVENTION

The present invention relates to an adhesive dressing sheet which is used for covering of a cut, fixation of an IV catheter, and so forth.

BACKGROUND OF THE INVENTION

An adhesive dressing sheet usually has a structure in which a polymer film having excellent skin fit properties is used as a substrate, an adhesive layer is provided on one side of the substrate and a peeling liner is temporarily provided on the adhesive layer as disclosed in, for example, JP-A-U-57-123129 and 58-124123. The term "JP-A-U" as used herein means an "unexamined published Japanese utility model application". In such adhesive dressing sheets, it is important that the sheet be accurately adhered to the skin while examining the skin portion to be covered. For this reason, it is considered that a bending line is previously provided on the peeling liner, and while bending the liner at the bending line and utilizing the bending state, the sheet is bonded to the skin while examining the affected part of the skin to be covered.

However, a polymer film 1' which is used as the substrate as shown in FIG. 7 is a thin film-like material having a low modulus to provide sufficient skin adhesion properties and therefore does not have an elasticity against bending force. Thus, as shown in FIG. 7, when a peeling liner 3' is peeled off up to a bending line 32', liner bending pieces 30', 30' expand, and only by application of a slight tensile stress, the liner remaining piece is inevitably continuously peeled off from a surface of an adhesive layer 2'. Therefore, careful handling is required and it is not easy to adhere the sheet while examining the affected part of the skin to be covered.

A dressing sheet in which a backing sheet is temporarily bonded to the back side of the polymer film 1' so that the polymer film 1' does not wrinkle at the time of bonding is also proposed as disclosed in, for example, JP-A-U-62-42814. In such dressing sheets, however, it is sufficient for the backing sheet to have supporting properties to the extent that the backing sheet bonds to the polymer film 1' and does not wrinkle and, therefore, the above problem due to insufficient bending elasticity as encountered in providing a bending line on the peeling liner and bending the liner cannot be avoided.

SUMMARY OF THE INVENTION

Accordingly, an object of the present invention is to provide a novel adhesive dressing sheet which can overcome the above-described problems.

The present invention provides an adhesive dressing sheet having a structure that an adhesive layer is provided on one side of a polymer film having a high flexibility and a peeling liner is provided on the adhesive layer, and on the other side of the polymer film, a flexible sheet is temporarily provided, wherein a bending line is provided on the peeling liner in a direction almost in right angles to the liner peeling direction, and the flexible sheet has self supporting properties such that when the liner is peeled off up to the bending line and bent, the liner bending piece does not expand to an angle of 90° or more.

BRIEF DESCRIPTION OF THE DRAWINGS

FIG. 1A illustrates an example of the present invention and is a plan view seen from the side of the peeling liner;

FIG. 1B is a cross sectional view taken in the plane of line I—I' in FIG. 1A;

FIG. 3 is a cross sectional view illustrating the state that the peeling liner is peeled off;

FIG. 4A illustrates another example of the present invention and is a plan view seen from the side of the flexible sheet;

FIG. 4B is a cross sectional view taken in the plane of line I—I' in FIG. 4A;

Figure 2A:
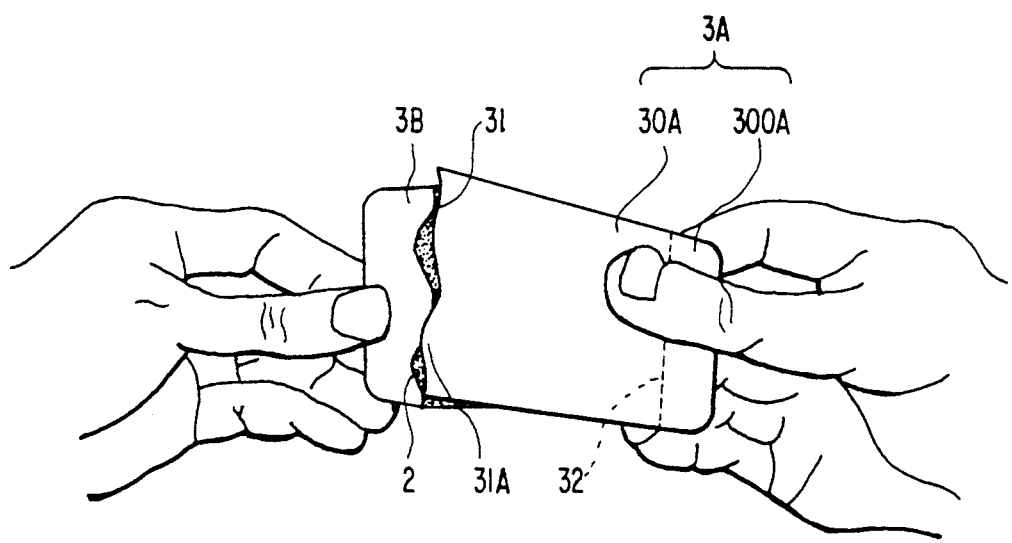
FIGS. 2A and 2B are views illustrating the manner of use thereof.

In the drawings, 1 indicates a polymer film; 2, an adhesive layer; 3, a peeling liner; 32, a bending line; and 4, a flexible sheet.

DETAILED DESCRIPTION OF THE INVENTION

The present invention is now explained in detail by reference to the drawings.

In FIGS. 1A and 1B, 1 indicates a polymer film which is obtained by molding a polyetherurethane, a polyester-urethane, an acryl polymer, a nylon derivative, elastomeric polyester, a mixture of polyester and polyurethane, or the like into a film having a thickness of about 20 to 150 $\mu$m and has such a high flexibility that 50% modulus is about 20 to 200 kg/cm$^2$. The film 1 desirably has a moisture permeability so as not prevent the respiration, of the skin after adhering the film to the skin. In FIG. 1, 2 indicates an adhesive layer of e.g., acryl, which is provided on one side of the film 1 and, if necessary, a desired drug is contained in the adhesive layer. In FIG. 1, 3 indicates a peeling liner temporarily provided on the layer 2, and for example, a peeling paper subjected to silicone treatment and having a Weight of about 80 to 200 g/m$^2$ is used. In the peeling liner 3, a cutting line 31 (e.g. cut) with a wave-like shape extending along the end 3b and in the edge direction of the edge 3b is provided, and the liner 3 is divided into divided pieces 3A, 3B by the cutting line 31. In the larger divided piece 3A, a straight bending line 32 (e.g. perforation) is provided along the other end 3a and in a direction almost parallel to the above cutting line 31, and the divided piece 3A is partitioned into a central portion 30A having a relatively large area and a side portion 300A. The direction in which the bending line 32 is provided is almost at right angles to the peeling direction (f) of the liner divided piece 3A. In FIG. 1, 4 indicates a flexible sheet fitted to the other side of the film 1. The sheet 4 is made of a material having a thickness of about 25 to 75 $\mu$m, and selected from plastic sheets, paper and so forth, so as to have self supporting properties such that when the liner divided piece 3A is peeled off up to the bending line 32 and bent, the liner bended part (divided piece 3A) does not expand to the angle of 90° or more.

Figure 2B:
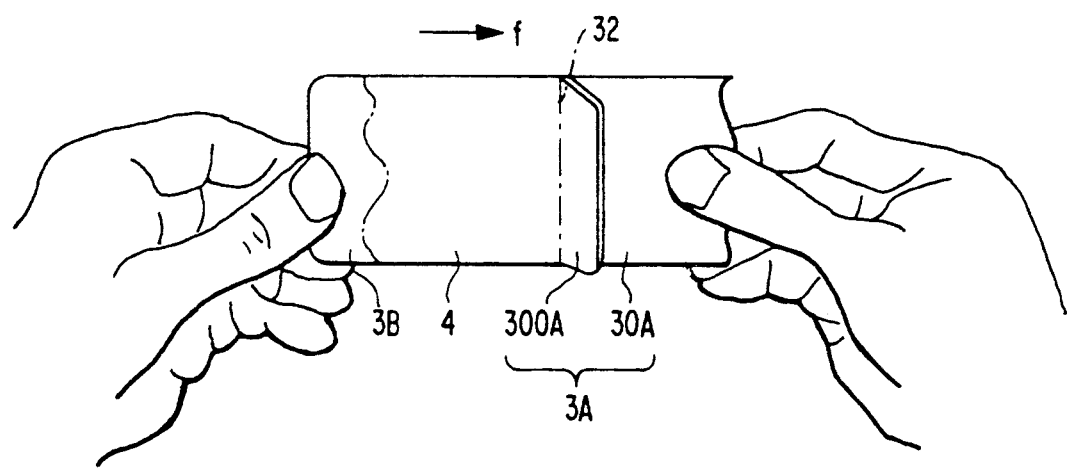

In the adhesive dressing sheet having the above-described structure, as illustrated in FIG. 2A, when the whole sheet is bent to the side of the flexible sheet 4, the peeling liner 3 is divided into the divided pieces 3A and 3B by the cutting line 31 portion. As illustrated in FIG. 2B, piece 3B portion of the divided pieces is held with fingers of one hand, and at the same time, the cut convex portion 31A of the larger divided piece 3A is held by fingers of the other hand and picked up to peel off from the sheet. When the larger divided piece 3A is peeled off up to the bending line 32, the divided piece 3A is bent at this part by the line 32. At this time, the great self supporting properties of the flexible sheet 4 exhibit repelling elasticity (y) against recovering force (g) of the remaining liner pieces (side portion 300A of divided piece 3A) and prevent the bent divided piece 3A from expanding to an angle $\theta = 90°$ or more. Thus, as illustrated in FIG. 3, even if a tensile stress is applied to the central portion 30A constituting the divided piece 3A, a stress acts on the side portion 300A not in the cleavage direction but in the shear direction and, therefore, the side portion 300A is not easily peeled off from the adhesive surface and peeling of the portion is temporarily stopped. Then, while examining the skin surface on which the sheet is bonded, the sheet central portion is bonded thereto at the adhesive layer 2 surface and, thereafter, the divided piece 3A is strongly pulled out. In this manner, the liner residual piece (side portion 300A) is removed from the layer 2 surface, and the entire surface of the layer 2 is adhered to the skin. The flexible sheet 4 which is made into one unit along with the polymer film 1 is peeled off and removed from the surface of the film 1, and adhering is completed without touching of fingers to the adhesive surface.

Figure 5:
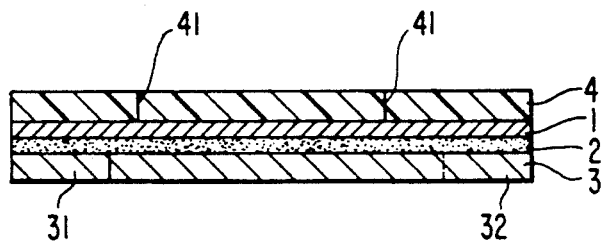
FIG. 5 is a cross sectional view illustrating another example of the present invention.
Figure 6:
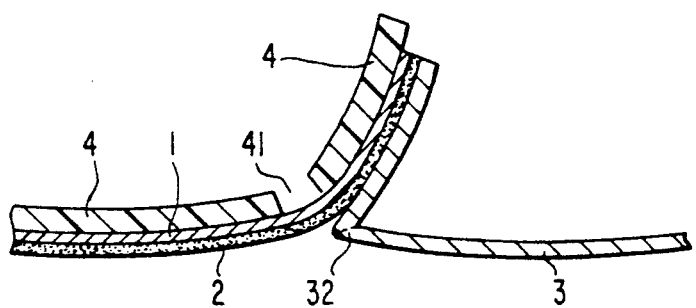
FIG. 6 is a cross sectional view illustrating the peeling liner-peeled off state in a case where a cutting line is provided on the flexible sheet at a position at which it overlaps with the bending line of the peeling liner.
Figure 7:
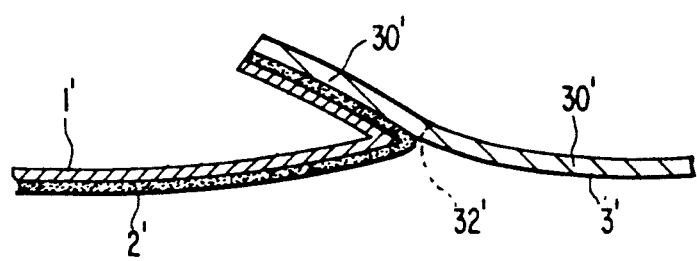
FIG. 7 is a cross sectional view of the conventional example illustrating the state that the peeling liner is peeled off.

FIGS. 4A, 4B and 5 illustrate other examples of the present invention. In FIGS. 4A and 4B, the cutting line 41 is provided in a direction in parallel to the bending line 32 on the flexible sheet 4 so as to divide the sheet into two portions 4A, 4B, and in FIG. 5, cutting lines 41 and 41 are provided so as to divide the flexible sheet 4 into three portions. If cutting lines are provided on the flexible sheet 4, when the whole sheet is attached to the skin surface, the sheet is bent according to the raised form of the skin surface, and there is formed a condition that the divided pieces 4A, 4B of the sheet 4 come to the surface from the cut line portion. Therefore, peeling and removal of the sheet becomes easy. For this reason, when a cutting line is provided on the flexible sheet 4, it is necessary for the cutting line to be provided at a location at which the line crosses with the bending line 32 of the liner 3, or at a location at which it is, as illustrated in the FIGS. 4A, 4B and 5, in a parallel condition and does overlap. If the cutting line overlaps with the bending line of the liner, the desired effects of the present invention are not exhibited. That is, the bending stress when the liner is bent at the bending line is concentrated at the bending line portion in the case of the flexible sheet 4. In the present invention, since the sheet 4 exhibits, as described above, great repression elasticity, the bending stress is rather concentrated at the cutting line portion and the sheet 4 is easily peeled off before adhering (FIG. 6) and, therefore, handling becomes difficult.

In the present invention, in order to facilitate that a position to be adhered can be easily confirmed in the adhering operation, it is desirable that polymer film 1, the adhesive layer 2 and the flexible sheet 4 be transparent.

In the present invention, peeling of the liner bent piece can be temporarily stopped by bending the liner at the bending line provided on the peeling liner. Therefore, even if a tensile stress is applied, the remaining piece of the liner is not continuously peeled off, the sheet can be accurately bonded by fingers while confirming the skin surface to be bonded, and the handling is easy.

While the invention has been described in detail and with reference to specific embodiments thereof, it will be apparent to one skilled in the art that various changes and modifications can be made therein without departing from the spirit and scope thereof.

We claim:

1. An adhesive dressing sheet comprising the following layers, in sequence,
   (a) a self-supporting flexible sheet with a thickness of about 25-75 μm, and having a cutting line which divides said sheet into a plurality of pieces;
   (b) a polymer film with a thickness of about 20-150 μm, and a 50% modulus of about 20-200 kg/cm$^2$;
   (c) an adhesive layer; and
   (d) a peeling liner having (1) a cutting line, and (2) a bending line provided almost at right angles to the linear peeling direction thereof, wherein the cutting line on said flexible sheet does not overlap the bending line on said peeling liner.

2. An adhesive dressing sheet as claimed in claim 1, wherein the polymer film, the adhesive layer and the flexible sheet are transparent.

3. An adhesive dressing sheet as claimed in claim 1 wherein said peeling liner is a paper subjected to silicone treatment and has a weight of about 80-200 g/m$^2$.

4. An adhesive dressing sheet as claimed in claim 1 wherein said film is moisture permeable.

5. An adhesive dressing sheet as claimed in claim 1 wherein said film is obtained by molding a polyurethane, a polyester-urethane, an acryl polymer, a nylon derivative, an elastomeric polyester, or a mixture of polyester and polyurethane.

6. An adhesive dressing sheet as claimed in claim 1, wherein said peeling liner is divided into a concave portion and a convex portion by a transverse sinusoidal cutting line.

7. An adhesive dressing sheet as claimed in claim 1 wherein said adhesive layer contains a drug.

8. An adhesive dressing sheet as claimed in claim 1 wherein the cutting line on said flexible sheet is parallel to the bending line on said peeling liner.

* * * * *